(12) United States Patent
Moan et al.

(10) Patent No.: US 6,911,194 B2
(45) Date of Patent: Jun. 28, 2005

(54) SKIN PREPARATION

(75) Inventors: Johan Moan, Oslo (NO); Robert Bissonnette, Longueuil (CA)

(73) Assignee: PhotoCure ASA, Oslo (NO)

(*) Notice: Subject to any disclaimer, the term of this patent is extended or adjusted under 35 U.S.C. 154(b) by 451 days.

(21) Appl. No.: 10/275,557

(22) PCT Filed: May 4, 2001

(86) PCT No.: PCT/NO01/00189

§ 371 (c)(1),
(2), (4) Date: Jan. 13, 2003

(87) PCT Pub. No.: WO01/85125

PCT Pub. Date: Nov. 15, 2001

(65) Prior Publication Data

US 2003/0133888 A1 Jul. 17, 2003

(30) Foreign Application Priority Data

May 10, 2000 (NO) .................................. 002428

(51) Int. Cl.⁷ ............................. A61K 7/42; A61K 7/44; A61K 7/00; A61K 31/195
(52) U.S. Cl. ........................... 424/59; 424/60; 424/400; 424/401
(58) Field of Search ........................... 424/59, 60, 400, 424/401; 514/561

(56) References Cited

U.S. PATENT DOCUMENTS 5,520,905 A    5/1996  Uhlmann et al.

FOREIGN PATENT DOCUMENTS

WO    WO 96/28412    9/1996

OTHER PUBLICATIONS

J.M. Menter et al, "Protection against photodynamic therapy (PDT)–induced photosensitivity by . . . fabric materials" Photodermatology Photoimmunology and Photomedicine vol 14 1998 pp 154–159.

Zhao–Hui Jin et al, "Treatment effects of transplanted squamous cell carcinoma by iradiations . . . of laser light . . . with endogenously–produced Pp–IX . . . " Photomed. & Photobiology v 8 1996 p 85–86.

Roar Sørensen et al. "Formation of protoporphyrin IX in mouse skin after topical application of . . . 5–aminolevulinic acid and its methyl ester" Proceedings of Photochemotherapy of Cancer and Other Diseases vol 3563 1999 pp77–81.

Clemens Fritsch et al "Preperative relative Porphyrin Enhancement in Solar Keratesis upon topical application of S–Aminolevulaic acid methylester"to Photochemistry Photobiology vol 68 1998 pp 218–221.

*Primary Examiner*—Shelley A. Dodson
(74) *Attorney, Agent, or Firm*—Christian D. Abel

(57) ABSTRACT

A skin preparation is described for protection against sunlight, containing UVA and UVB-absorbent agents, an ALA derivative and conventional supplementary substances, together with the use of the preparation.

15 Claims, 12 Drawing Sheets

Figure 1A:
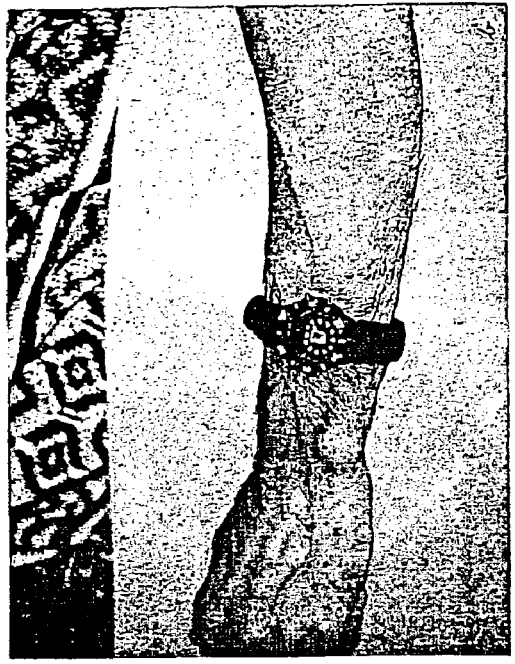
Figure 1A:
Figure 1B:
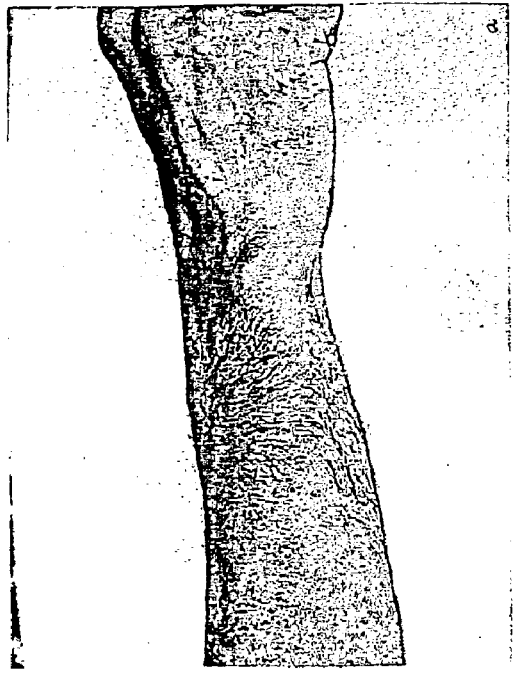
Figure 1B:

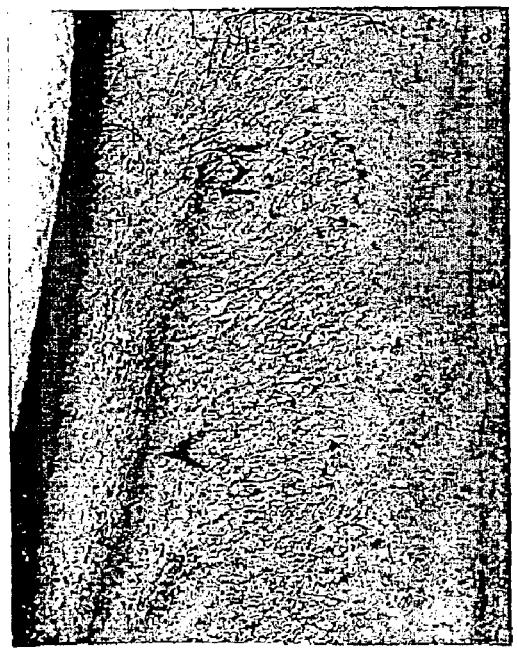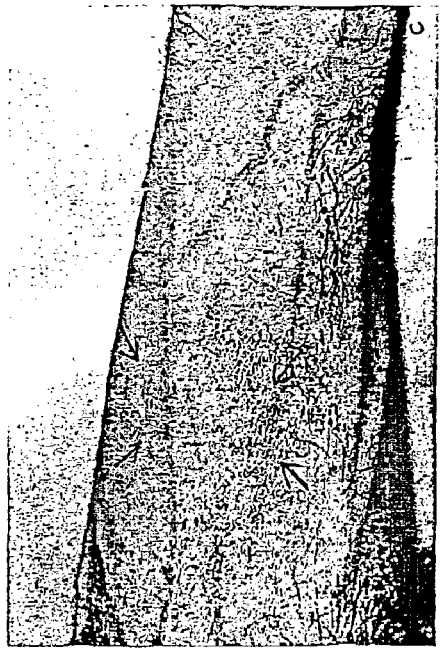
FIG. 6A
FIG. 6B

SKIN PREPARATION

The present invention relates to a skin preparation containing derivatives of δ-aminolevulinic acid (ALA) and substances which absorb UVA rays and UVB rays, a method for protecting the skin of mammals, and the use of the preparation for sun protection.

All three skin cancer types, basal cell cancer (BCC, 10,000 per annum in Norway), squamous cell carcinoma (SCC, 6–700 per annum in Norway) and cutant malignant melanoma (CMM, 900–1,000 per annum in Norway) are mainly caused by solar radiation. This is clearly demonstrated by their pattern of localisation on the body and by the north-south gradient in the incidence (e.g. three times more frequent on the south coast of Norway than in northern Norway). For decades the incidence of skin cancer has been increasing more rapidly than the incidence of most other types of cancer, and there is little doubt that this is due to increased sunbathing, more travel to southern destinations and more use of solaria. A similar increase to that in Norway can be observed in most western countries with a white population. The increase in sunbathing is probably due primarily to culturally-based pressure, a tanned skin being a sign of affluence, well-being and good health.

Sun creams with added "sun factor" which absorbs UVB (wavelengths between 280 and 320 nm) and UVA (wavelengths between 320 and 400 nm) are widely used over large parts of the world. These sun creams, however, do not provide complete protection against such radiation, but have the effect of reducing the dose to a greater or lesser extent.

The use of sun creams with sun factor, however, does not seem to have reduced the incidence of skin cancer. Nor does the opposite seem to be the case. It may be assumed that since the sun creams offer protection against sunburn, they give a false feeling of security, with the result that people are tempted to stay out in the sun longer than they should. This offsets the protection provided by the sun cream of increased exposure time.

Recent research shows that the sun creams probably do not provide as good protection against impairment of the immune system and the development of malignant melanoma as they do against sunburn. This is associated with the fact that while sunburn (erythema) is mainly due to UVB, it appears that the UVA radiation, of which there is 30–50 times more than there is of UVB radiation in the solar spectrum, causes both impairment of the immune system and the development of melanoma. This appears to apply to shortwave, (blue) visible light, which is not stopped by the sun creams now in use. Since the action spectra for pigmentation, sunburn and skin cancer are almost identical in the UVB range, while UVA and visible blue light dominate the action spectrum for malignant melanoma, it is therefore not possible to achieve pigmentation (a tan) in the traditional manner, even with the use of cream with "sun factor", without also being exposed to an increased risk of skin cancer. Both UVB and UVA induce synthesis of melanin, the pigment which makes the skin tan. Melanin absorbs both UVB and UVA and thus has a protective effect. This protection, however, is not sufficient to prevent the development of skin cancer in people with fair skin (types I–III).

There is therefore a great need for a skin cream which protects against the sun's harmful effects as set forth above, while providing an acceptable pigmentation of the skin.

In both U.S. Pat. No. 5,520,905 and EP 0 633 017 A2 cosmetic and dermatological composition is known which contains absorbent agents for UVA rays and UVB rays in addition to a combination of δ-aminolevulinic acid (ALA) and at least one antioxidant. This composition is stated to provide protection against skin damage due to light exposure. From Photochemistry and Photobiology, 1997, 66(4): 493–496 it is furthermore known that when ALA was applied topically to naked mice and exposed to treatment with simulated solar UV radiation, the exposed areas became erythematous, in addition to which photo-induced carcinogenesis was delayed. Subsequent experiments have shown that light exposure of ALA, which induces production of protoporphyrin IX (PpIX) spreads over skin areas which are considerably larger than the area where ALA was initially applied (Proc. Photochemotherapy of Cancer and Other Diseases, Volume 3563, 1999). Together with the observation that the light exposure of the naked mice in Photochemistry and Photobiology (1997, 66(4): 493–496) clearly caused discomfort and pain, judged on the basis of the animals' irritability, and the widespread area of skin involved when using ALA, the use of ALA in skin cream seems to have substantial side effects.

As documented in the following, application of ALA containing sun cream over large skin areas will lead to a widespread distribution of the compound in the body. It is well known in the art of porhyria diseases that accumulation of ALA in the body may produce side effects since it is known that ALA may be both liver toxic and neuro toxic.

It is therefore an object of the present invention to provide a sun protection composition without the above-mentioned side effects.

This object is achieved with the present invention, characterized by that which is set forth in the claims.

The present invention relates to a skin preparation which takes advantage of the protective effect which ALA derivatives can provide in connection with sunlight. The invention thus relates to a preparation based on a standard, commercial base to which is added a UVB-absorbent agent, a UVA-absorbent agent and an ALA derivative. The derivative is chosen from the group comprising ester and amino derivatives of ALA. Commercially available and tested UVB and UVA-absorbent agents are employed in concentrations which provide a protection factor of at least 20. Of ALA derivatives a concentration is used which is 1000 to 50 times lower than that used for photodynamic treatment of skin cancer (20% on a weight basis).

The cream according to the invention thereby has the following effect:
1) It eliminates both UVB and UVA radiation and prevents ordinary skin cancer development.
2) It stimulates melanogenesis in the skin by the production of PpIX from the ALA derivative, thus making it possible to become tanned without the risk of skin cancer.
3) It has an anti-carcinogenic effect (counteracts cancer development).

The preparation is applied like ordinary sun cream/oil before going out in the sun.

The present inventors have carried out research which demonstrates that melanin synthesis can be further stimulated by applying to the skin derivatives of δ-aminolevulinic acid (ALA), especially esters or amino derivatives. ALA derivatives have a tanning effect in an entirely different way from UVB and UVA. Porphyrin synthesis is stimulated by putting to use the skin cells' biosynthesis of haem. Small quantities of protoporphyrin IX (PpIX) thereby accumulate in the skin cells. PpIX is a photosensitising substance which causes oxidative cell damage during exposure. PpIX is formed in the cells' mitochondria, but is not absorbed in the nucleus. During sunbathing, therefore, PpIX will not cause any genetic damage which may form the basis for cancer development, as is the case with UVB and UVA. The oxidative cell damage which arises when skin is exposed after treatment with ALA derivatives stimulates melanin synthesis, i.e. pigmentation. The detailed biosynthesis of melanin is not known, either for UVB, UVA or for exposure to PpIX, but it is assumed that UVB works via DNA damage.

It bas been shown that the presence of small quantities of PpIX generated by ALA in the skin of mice irradiated with UV has anti-carcinogenic effect. PpIX inhibits the development of UV-induced skin cancer in animals. ALA derivatives also produce PpIX.

ALA derivatives thereby have a doubly protective effect:
1) They stimulate, i.e. accelerate pigmentation (which has a protective effect against UVB and UVA) without causing DNA damage which in turn can lead to cancer development. Thus fluorescence microscopic experiments demonstrated that the active substance formed by these creams, PpIX, does not exist in cell nuclei where there is DNA, but in cytoplasm, principally in the mitochondria (data not enclosed). Furthermore, patients with the inherited disease erythropoietic protoporphyria (EPP) have large amounts of PpIX in their skin. No cases of skin cancer are reported in these patients. Even though the disease is rare, reports should be expected of skin cancer in EPP patients over a long period of time and in many countries, since their skin is monitored with particular attention.
2) ALA derivatives have an inhibiting effect on the development of skin cancer. Small amounts of UVB and UVA will pass through any sun cream regardless of the protection factor. The PpIX formed in the skin by ALA derivatives will protect the skin against UVB and UVA-induced cancer development. In addition, the present inventor has observed that the skin reaction on light exposure of ALA derivative-treated skin is restricted to those areas which are covered by the composition. It is a surprising and positive effect compared to the effect of ALA. Moreover, ALA esters have completely different pharmacokinetics and are anti-carcinogenic compared to ALA.

In summary ALA esters have some extremely surprising advantages over ALA: When ALA is applied on the skin of mice, it goes rapidly into the circulation and induces PpIX in the whole mouse, in skin and all over, in liver, in intestine and so on. ALA esters on the other hand, do not enter the circulation, and produce PpIX only on the skin location where they were applied. This is surprising, since the esters are more lipophilic than ALA itself and are thus expected to penetrate more easily through the epidermis and into the circulation. Furthermore, their kinetics of PpIX production are different from that of ALA. While inducing pigmentation during light exposure, they seem to act more superficially in the skin than ALA does. These differences make them better suited for sun cream use than ALA.

According to the invention a preparation or a composition is provided which is applied to the skin in connection with sunbathing, and which promotes the formation of skin pigments, protects against the carcinogenic effect of UVA and UVB rays and has an anti-carcinogenic effect. The preparation comprises UVA-absorbent agents, UVB-absorbent agents, ALA derivative, pharmaceutically acceptable carriers, emulsifiers, diluents and preserving agents which are suitable for dermal topical application.

UVB and UVA-absorbent agents are chosen from known, commercially available substances which are approved for use in sun creams, such as oxybenzenes, methoxycinnamates, salicylates, benzophenone derivatives, phenylbenzidine derivatives and methoxybenzoyl derivatives, in addition to physical filters such as titanium dioxide, zinc oxide, calcium carbonate, kaolin, magnesium oxide, iron oxide or talc. Compounds are preferably chosen which infiltrate the circulation to the least possible extent, and in concentrations which provide a protection factor of at least 20.

The ALA derivatives are found in concentrations from 0.02% to 0.4%, based on the weight of the complete composition.

The composition can be formulated as oil, gel, cream, ointment, paste, spray, sticks or in other forms known in the art. The formulations also contain the active compounds, thickening agents, gelling agents, suspension agents, emulsifiers, dispersing agents and dyestuffs well known to a person skilled in the art of pharmacy.

A preferred embodiment comprises a preparation on an ordinary commercial basis, where the concentrations of UVA and UVB-absorbent agents provide a protection factor of at least 20 and the ALA derivative is an ALA ester, e.g. ALA methylester, with a concentration from 0.02% to 0.4% based on the weight of the cream.

The invention will now be supported by examples and figures, which in no way will be limiting for the scope of protection, defined by the attached claims.

FIG. 1 Human hands with ALA and ALA methyl ester containing cream applied on the skin surface (A:ALA; M:ALA methyl ester). The lower panels (B) are enlargements of the corresponding upper panels (A). In the left panels the skin was exposed to light (350–400 nm) for 5 min., in the right panels the light exposure was 1 min. The exposed areas are marked with broken circles.

Figure 2:
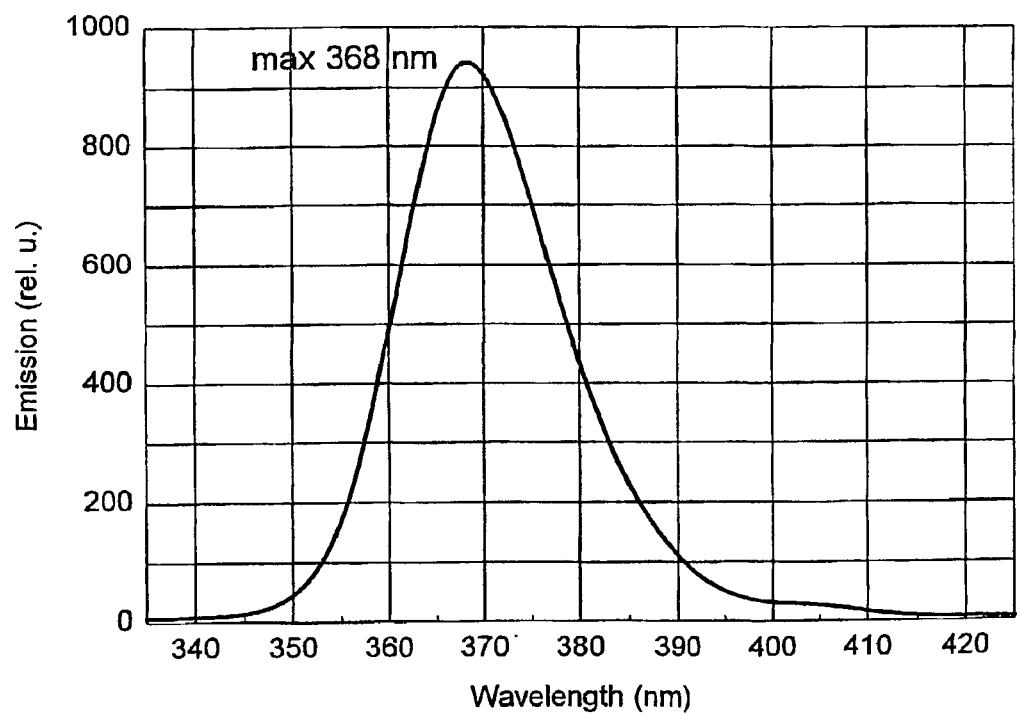

FIG. 2 Light emision (rel.u) versus wave length (nm) of the black light used in FIG. 1.

Figure 3A:
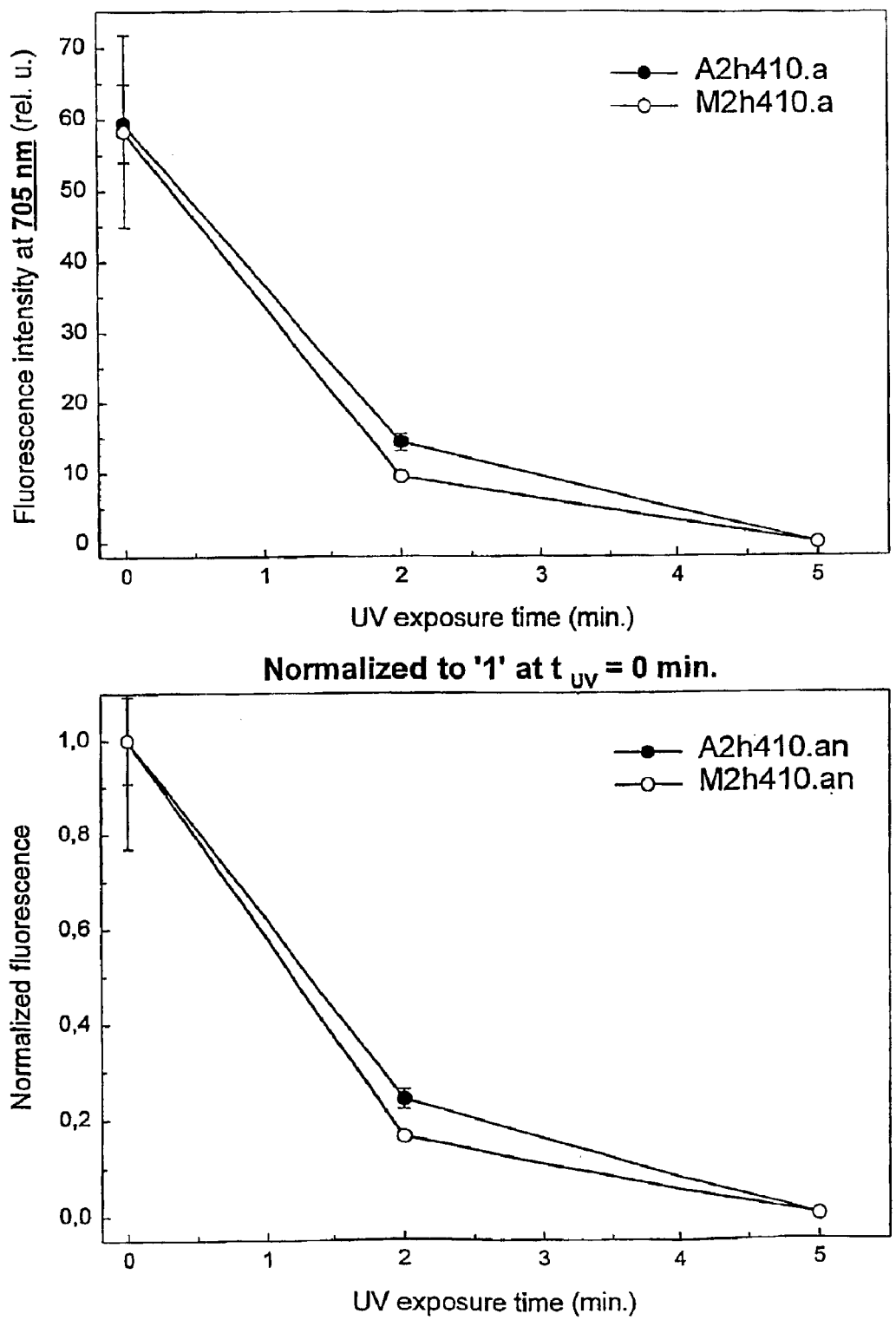
Figure 3B:
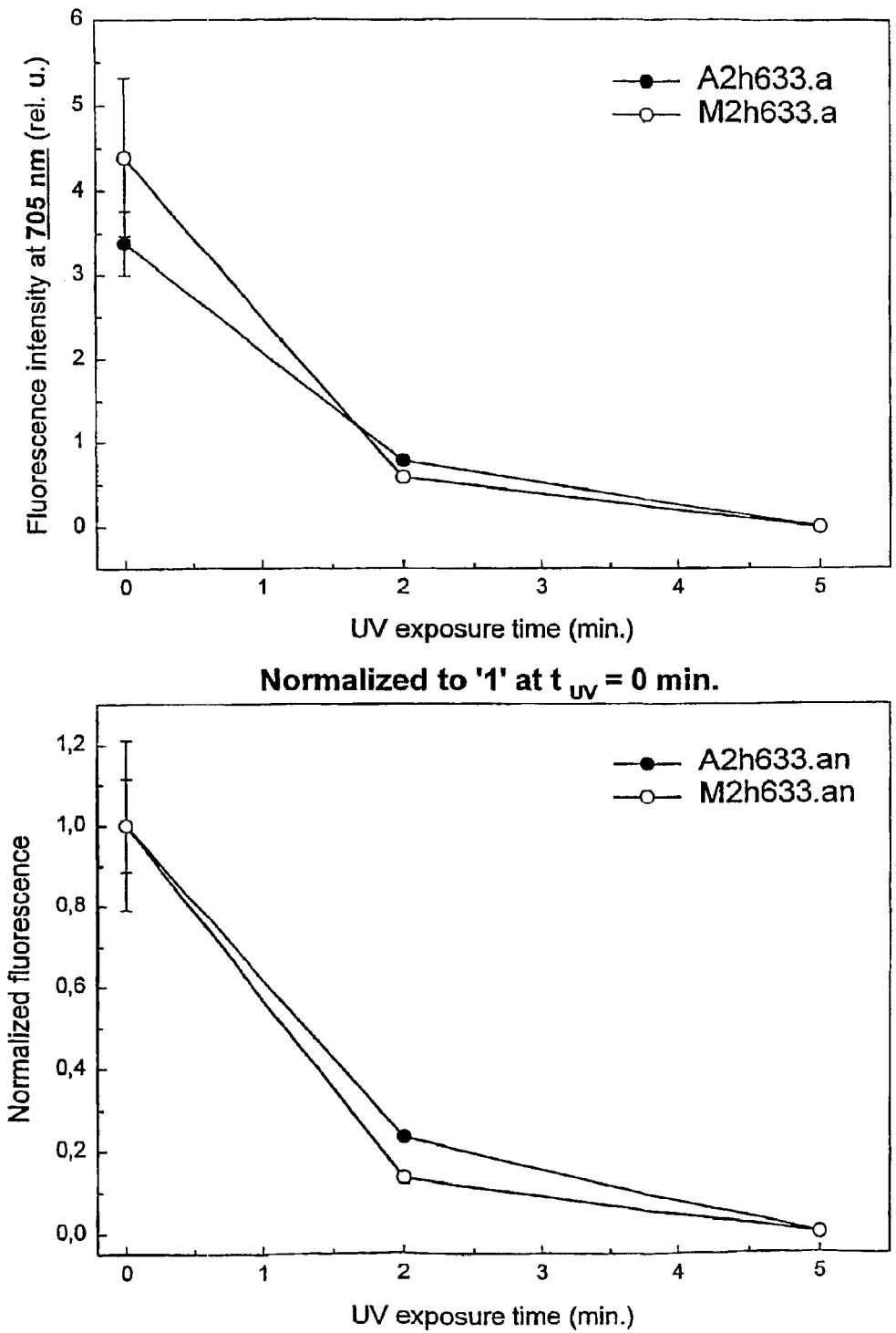

FIGS. 3A, B PpIX photo bleaching under UV exposure at 368 nm. ALA (A) and ALA methyl ester (M) were topically applied for 2 hours on the skin of the nude rat. Fluorescence kinetics for exitation wavelength was 410 nm. The lower panel shows normalized intensities in that the fluorescence intensity at 0 time is set to 1.

Figure 4A:
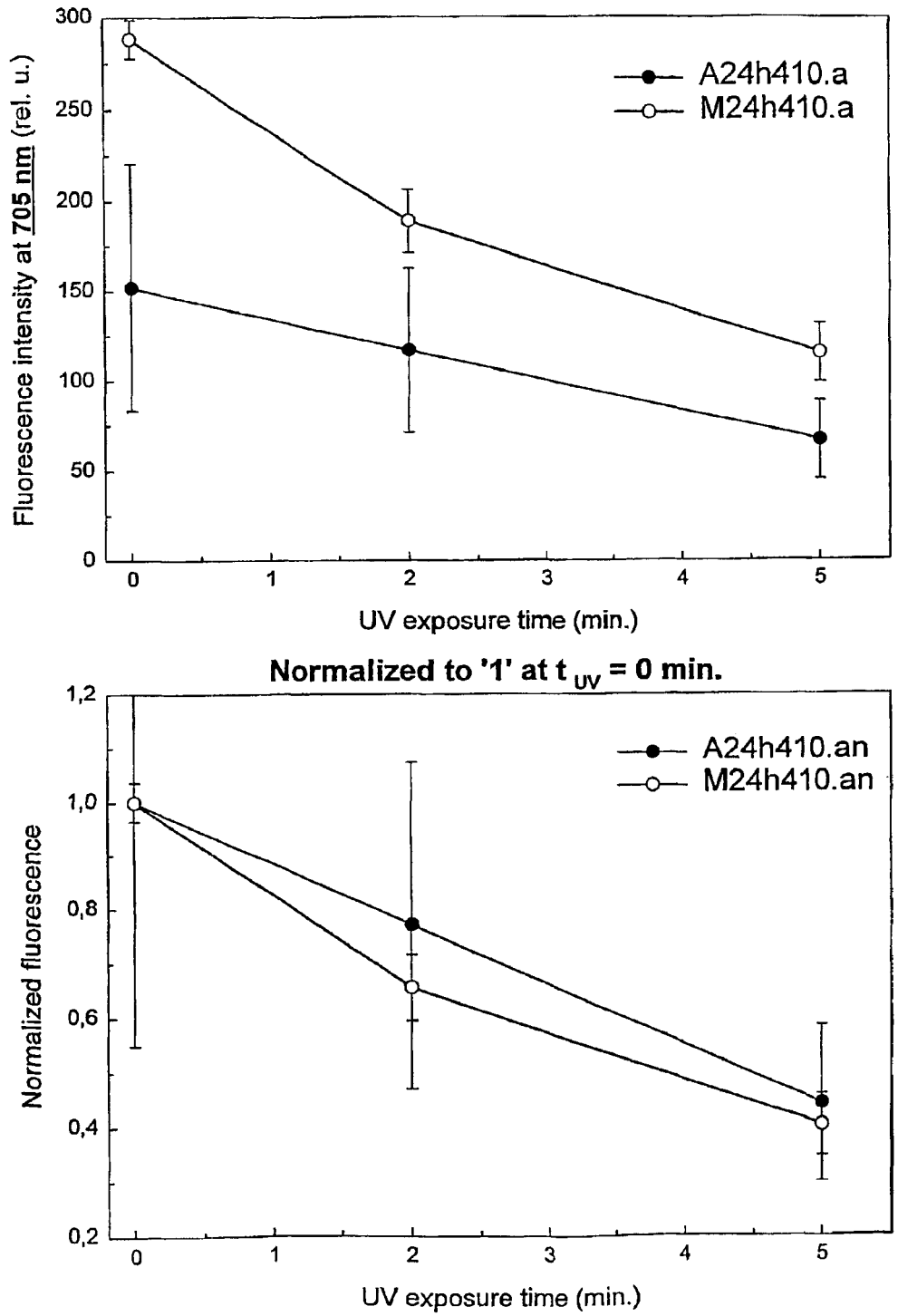
Figure 4B:
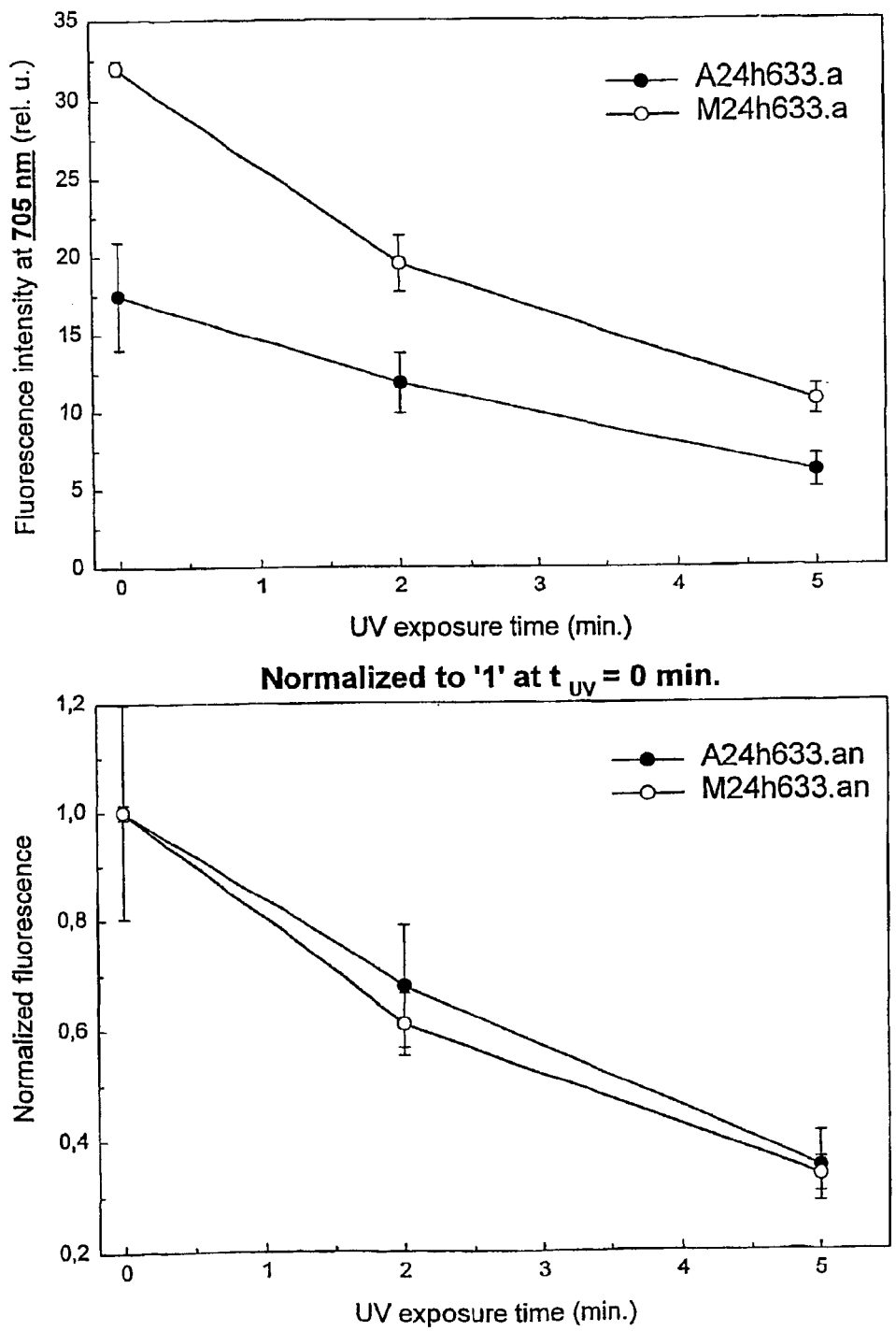

FIGS. 4A, B PpIX photo bleaching under UV exposure as in FIGS. 3A, B, wherein the ALA and ALA methyl ester containing cream was applied for 24 hours.

Figure 5:

FIG. 5 Hairless mouse with a cream containing ALA methyl ester applied between the arrows, after exposure for 1 min. laser light, wherein the light exposure was repeated 10 times in 2 weeks.

FIG. 6 Upper panels (A). Human arms with ALA (A) and ALA methyl ester (M) containing cream was applied for 4 hours whereupon the cream was removed and the arm light exposed for 3 min. Lower left panel (B). Human arm one week after a single non erythemogenic treatment within the arrows. Lower right panel (B). Human arm 2 weeks after light exposure (20% ALA; 1 min. light).

Figure 7:
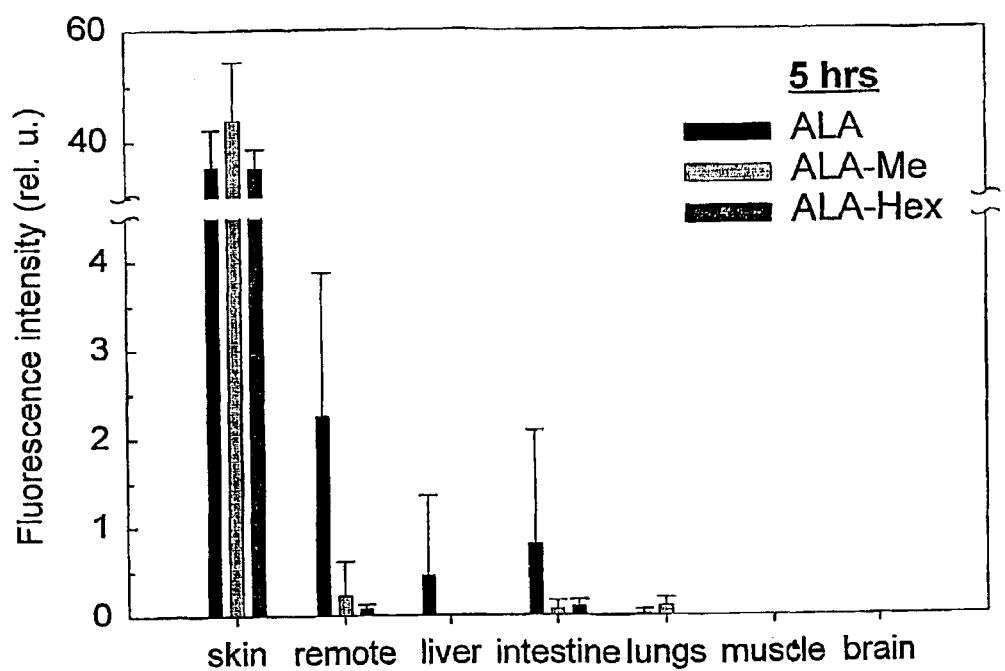

FIG. 7 Tissue distribution of PpIX fluorescence intensity in mice after topical 5 h application of 20% ALA/ALA-Me/ALA-Hex cream.

Figure 8:
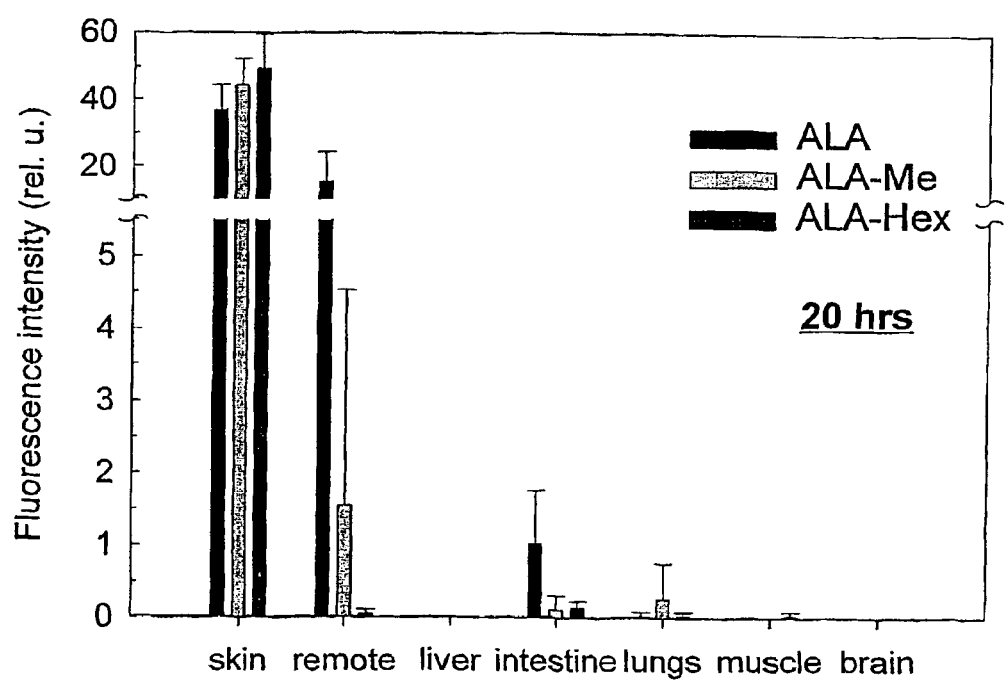

FIG. 8 Tissue distribution of PpIX fluorescence intensity after topical 20 hr application of 20% ALA/ALA-Me/ALA-Hex cream. The fluorescence was measured by LS 50B spectrofluorimeter.

Figure 9:
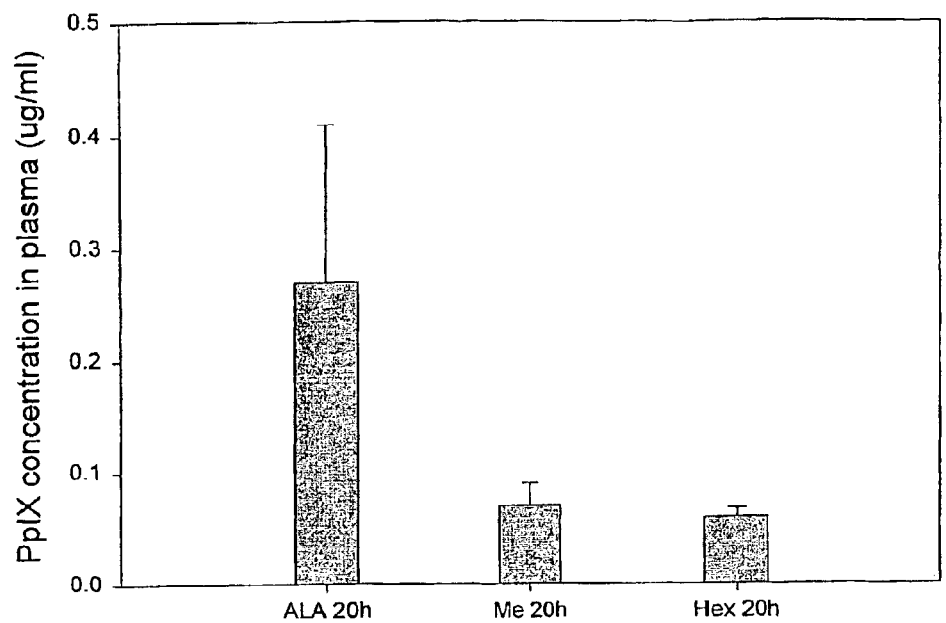

FIG. 9 Concentration of PpIX in plasma 20 hr after topical application of 20% ALA, ALA-methyl ester (Me) or ALA-hexyl ester (Hex).

Figure 10:
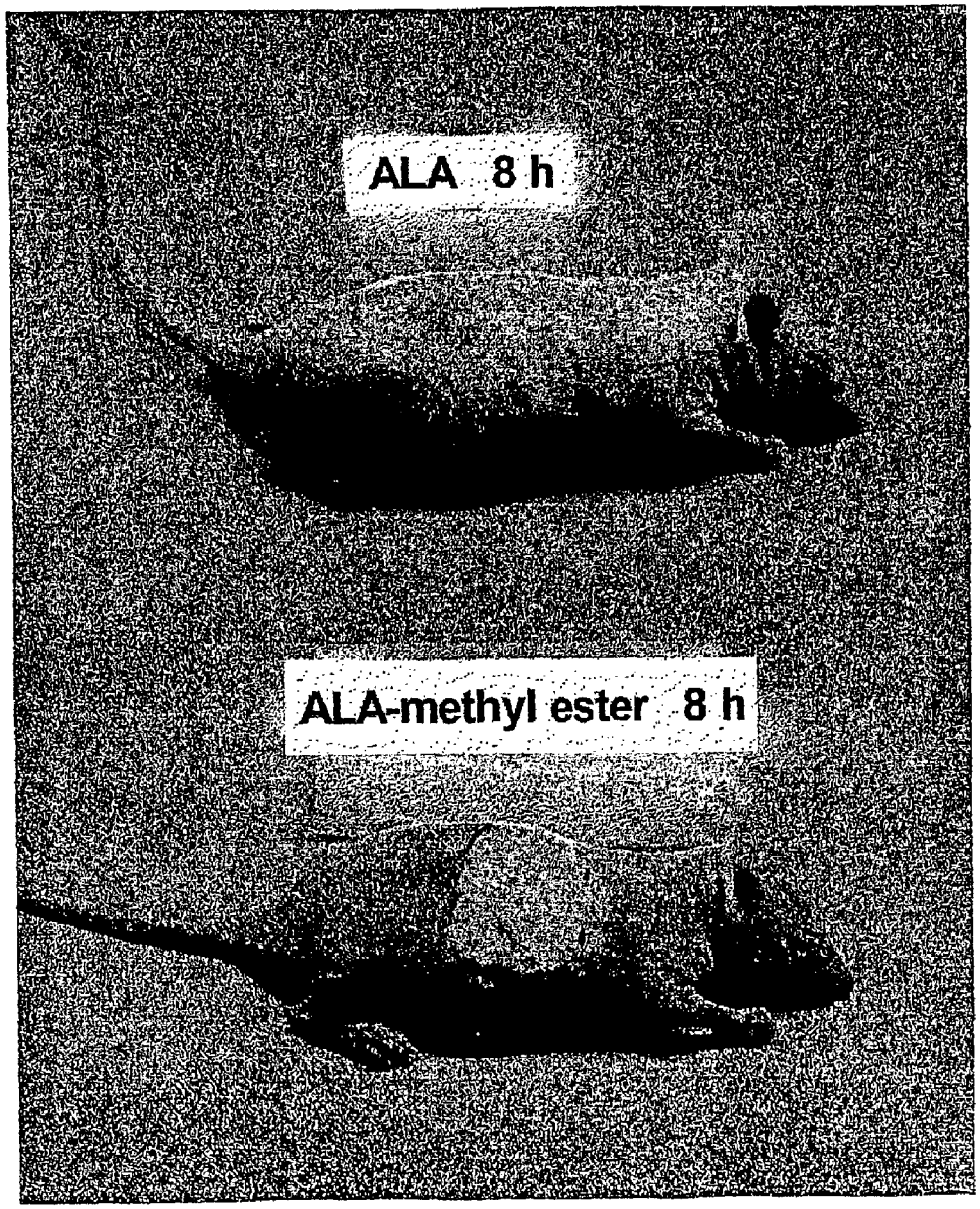

FIG. 10 Nude BALB/C mice photographed 8 hours after creams containing ALA and ALA methyl ester were applied to areas of the skin marked with broken circles.

EXAMPLE 1

Animal experiments show that UV induction of skin cancer is delayed by ALA creams producing PpIX (Photochemistry and Photobiology, 1997, 66(4): 493–496) as creams containing ALA esters.

EXAMPLE 2

This example demonstrates that ALA penetrates deeper into human skin, and the resulting erythema covers a larger skin surface that after application of ALA methyl ester.

Experimental

A high concentration of ALA and ALA-methyl ester (20%, Sigma) in a cream (Unguentum Merck) was applied to a circular area of 1 cm diameter for 5 hours on both hands of a person, FIGS. 1(A, B). A means ALA, M means ALA-methyl ester. The areas of application are shown by the dotted circles on the figure. The cream with the drugs were carefully washed away and the areas were exposed to ordinary blacklight from a fluorescence tube. The wavelengths of the light fall within the region 350–400 nm, FIG. 2. An exposure of 5 minutes was given to the left hand and an exposure of 1 minute was given to the right hand. Both these exposures are much larger than would be experienced by a sun cream user, but were chosen to demonstrate the difference in penetration depth between ALA and ALA-methyl ester.

Findings

The large exposures given here induce, as intended for demonstration, erythema spreading out from the area of application. The spreading was significally more pronounced for ALA than ALA-methyl ester. For ALA the erythema was circular, covering both the upper and the lower part of the hand, while for ALA methyl ester erythema developed only in a half-circle in the upper part of the hand where the skin is thinner according to well established physiological knowledge. The fluorescence pattern of PpIX was clearly seen and coincided with the erythema (data not shown).

Conclusion

ALA seems to penetrate thicker skin and induce PpIX deeper than ALA methyl ester is able to do. This is surprising in view of the fact that ALA methyl ester is the most lipophilic one of the two drugs. For application in a sun cream ALA methyl ester has therefore a strong advantage since it would have a lower potential to penetrate into the blood.

EXAMPLE 3

This example demonstrates differences in photobleaching rates of PpIX produced in the skin of nude rats after application of ALA and ALA methyl ester.

ALA and its methyl ester derivative were applied to the skin of nude rats (RWT Nu/Nu) for 2 (FIGS. 3a and b) and for 24 hours (FIGS. 4a and b). Then the skin was exposed to light in a wavelength band around 368 nm. The intensity was of the order of 20 W/m$^2$. It can be seen that the PpIX produced from ALA-Me is faster bleached than PpIX produced from ALA. This is consistent with the result of Example 2, and indicate that ALA produces PpIX deeper in rat skin than ALA-Me does.

EXAMPLE 4

This example presents evidence supporting that both ALA and ALA derivates induce pigmentation in mouse skin and human skin.

Experiment A

ALA methyl ester (1% in Unguentum Merck cream) was applied to the skin of C3H/Tif hairless mice. One hour after the application, the mice were exposed to light for 1 min (red laser light, 100 m/Wcm$^2$, 633 nm). No erythema was observed. The treatment was repeated 10 times within 2 weeks.

Experiment B

ALA and ALA derivatives in cream was applied to different areas on the forearm of a person. Four hours afterwards the cream was removed and the arm was exposed to black light, 380 nm, for 1–5 min. The skin of the arm was examined for two weeks.

Results

A. The skin of the mice that were exposed to drug and light was gradually pigmented. The skin outside the spot of application of drug did not change in colour nor in morphology (FIG. 5).

B. High doses of light (3 min) and drug (20%) led to erythema as exemplified for ALA (A) and ALA methyl ester (M) in FIG. 6 upper panels (A). Lower doses of drug and light did not give observable erythema, however, one week after such a low dose of single nonerythemogenic treatment of ALA a clearly visible pigmentation (melanogenesis) was evident (FIG. 6, lower left panel area marked by arrows) (B). A slightly erythemogenic light exposure (20% ALA, 1 min light) also led to later pigmentation as exemplified on the lower right panel of FIG. 6 which is taken 2 weeks after light exposure (areas marked with A and arrows). The light exposure gave no reaction outside the area of drug application which is shown by arrows. Neither did drug application alone give any effect.

Conclusion

Topical application of ALA or ALA derivatives mouse and human skin followed by light exposure leads to melanogenesis (brown pigmentation. High doses of drug and light gives erythema. Pigmentation can be achieved both by erythemogenic single exposures and repeated nonerythemogenic exposures.

EXAMPLE 5

This example demonstrates that topical application of ALA results in a clearly more widespread production of PpIX than topical application of ALA derivatives.

ALA, ALA methyl ester and ALA hexyl ester containing cream was applied locally on the skin surface of hairless mice. Fluorescence intensities were used as indications of the concentration of PpIX on the application site (skin), in remote skin spots, in liver, intestine, lungs, muscle and brain and plasma.

5-aminolevulinic acid (ALA) and 5-aminolevulinic acid methyl ester (ALA-Me) were purchased from Sigma. St. Louis, Mo. 5-aminolevulinic acid hexyl ester (ALA-Hex) was obtained from PhotoCure AS (Oslo, Norway).

A cream was prepared using 20% (wt/wt) ALA, ALA-Me or ALA-Hex in an ointment (Unguentum, Merck, Darmstadt, Germany). Approximately 0.2 mg of the freshly prepared cream was applied on a single spot of 1 cm diameter on normal skin of each mouse. An adhesive dressing (OpSite Flexigrid, Smith and Nephew Medical, LTD, Hull, England) with a punched hole of 1 cm in diameter was first put on the skin. Then the cream was applied on the skin in the punched hole and covered with another similar dressing. 20 hours application time was used.

Female Balb/c athymic nude mice were obtained from Bomholt Gaard (Ry, Denmark). At the start of each experiment, they were 7–8 weeks old and weighed 18–25 g. Three mice were housed per cage with autoclaved filter covers in a room with subdued light at constant temperature (24–26° C.) and humidity (30–50%). Food and bedding were sterilized and the mice were given tap water ad libitum in sterilized bottles. For proper application of the cream, anaesthesia, hypnorm dormicum (approximately 4 ml/kg body weight), was i.p. injected into the mice. The mice woke up within 1 hr and appeared normally active during the ALA application.

Determination of PpIX Concentrations in Tissues

The method for determining the amounts of PpIX in tissues was described previously (Ma et al., 1998). Briefly, immediately after tissues collection, the fresh tissue samples were rinsed twice in PBS, blotted dry on clean paper, weighed and then brought into suspension in a solution of 1% SDS in 1 N perchloric acid/methanol (1:1 v/v) by means of an Ystral (Dottingen, Germany) mechanical homogenizer. After homogenization, tissue suspensions were frozen, thawed, sonicated, diluted in the same solvent and centrifuged. Levels of PpIX in the supernatants were quantitatively determined by recording fluorescence emission spectra of the samples using a Perkin-Elmer (Norwalk, Conn.) LS 50B spectrofluorimeter. The excitation wavelength was 407 nm, the slit width corresponded to a resolution of 15 nm and the emission wavelength was scanned from 550 to 700 nm. A cut-off filter was used to remove scattered light of wavelengths shorter than 515 nm from the light reaching the detection system of the spectrometer. Concentrations of PpIX in the samples were determined by adding a known amount of the drug (internal standard) comparable to that already present in the extraction medium and recording the emission spectra once more. The concentrations are given in micrograms PpIX per gram wet tissue.

PpIX Concentrations in Plasma

Immediately after mice were killed, whole blood was drawn directly from the right atrium of the heart. The total volume of blood obtained from each mouse was approximately 0.2 ml and was selected in EDTA-treated microtubes. The red blood cells were fluorimetrically determined as described above.

As demonstrated in FIGS. 7 and 8 ALA produced significantly more PpIX outside the application site, both after 5 hrs application time (FIG. 7) and after 20 hrs application time (FIG. 8), compared to ALA methyl ester. Correspondingly the concentration of ALA in plasma was higher than both ALA methylester and ALA hexylester (FIG. 9).

EXAMPLE 6

This Example Demonstrates that Contrary to ALA; applied ALA methylester is confined to the skin area where it is applied.

Cream containing 20% ALA and 20% ALA methyl ester was applied on the area marked by broken circles (FIG. 9) on the skin of nude BALB/c mice and photos were taken under UV lamp illumination after 8 hours. The photos show a marked difference in localization of protoporphyrin IX (PpIX) fluorescence. ALA methyl ester has produced PpIX only in the area where the cream was applied while PpIX produced from ALA is localized all over the skin. This demonstrates that ALA is distributed by the blood (FIG. 9) to the whole body while ALA methyl ester produced PpIX is localiced only in the part of the skin where the ester was applied.

EXAMPLE 7

This Example Demonstrates that ALA butyl ester and ALA hexyl ester applied on the forearm skin of a caucasian man produced less erythema than ALA.

A cream (Unguentum, Merck) containing 20% ALA, ALA butyl ester and ALA hexyl ester respectively, was applied on three separate areas on the skin of the forearm of a Caucasian man. Two hours later the skin areas were exposed to UVA light from a black light lamp for 5 min. Twenty four hours later a significant pronounced erythema was observed in the ALA area, while significant but weaker erythema was observed for ALA butyl ester and ALA hexyl ester (data not enclosed).

The content of PpIX produced in the skin areas was assessed by measuring the fluorescence emission spectra. Corresponding to the observed erythemas the ALA demonstrated the highest concentration of PpIX, while it was smaller in the ALA butyl ester area and smallest in the ALA hexyl ester area.

EXAMPLE 8

This example demonstrates that ALA methylester prevents skin cancer induced by UV radiation.

The ability of multiple photodynamic therapy (PDT) sessions with topical ALA methylester (ALA-Me) to prevent skin cancer induced by ultraviolet radiation (UV) was studied in the SKH1 hairless mouse. Groups of 20 mice were exposed 5 days per week to UV from FS20 tubes. One group was treated weekly with 8% topical ALA-Me followed 2 hours later by 1.2 J/cm$^2$ of light from a slide projector, The number, location, and size of skin tumors were registered weekly. Other study groups included: mice treated with 8% ALA-Me and not exposed to light, mice exposed to UV and vehicle, mice exposed to topical ALA-Me and light but not UV, as well as mice exposed to UV with half of their bodies treated with 8% ALA-Me and half of their bodies treated with the vehicle. ALA-Me-PDT induced a significant delay in the time when the first tumor appeared as compared to mice only exposed to UV ($p<0.0001$). After 26 weeks of UV exposure large tumors ($\geq 4$ mm) were present in 14 mice of the UV group as compared to only one mouse in the UV-ALA-Me group. In mice treated on one side with ALA-Me and on one side with the vehicle, the delay in tumor appearance was observed only on the side treated with ALA-Me, suggesting that a local rather than a systemic effect is responsible for this phenomenon. In vivo fluorescence spectroscopy and quantitative fluorescence microscopy showed that there was a preferential accumulation of protoporhyrin IX in tumors as compared to adjacent UV exposed skin and normal skin at the time of light exposure. In conclusion, topical ALA-Me-PDT delayed the appearance of UV-induced skin tumors as well as the incidence of large tumors without increasing mortality or morbidity.

What is claimed is:

1. A skin preparation with anti-carcinogenic and sun-protection effect containing UVA and UVB-absorbent agents, characterized in that said preparation comprises a derivative of δ-aminolevulinic acid (ALA) in an ordinary commercial basis with conventional supplementary substances.

2. A skin preparation according to claim 1, wherein said preparation has a sun protection factor of at least 20 and the concentration of the ALA derivative is from 0.01% to 1%, based on the weight of the preparation.

3. A skin preparation according to claim 2, wherein the concentration of the ALA derivative is from 0.02% to 0.4%, based on the weight of the preparation.

4. A skin preparation according to any one of claims 1–3, wherein said UVA and UVB-absorbent agents are selected from the group consisting of oxybenzenes, methoxycinnamates, salicylates, benzophenone derivatives, phenylbenzidine derivatives and methoxybenzoyl derivatives and physical filters, such as titanium dioxide, zinc oxide, calcium carbonate, kaolin, magnesium oxide, iron oxide or talc.

5. A skin preparation according to any one of claims 1–3, wherein the ALA derivative is an ester derivative or amino derivative.

6. A skin preparation according to claim 5, wherein the ester derivative of ALA is a methylester.

7. A skin preparation according to claim 5, wherein the ester derivative is a butylester.

8. A skin preparation according to claim 5, wherein the ester derivative is a hexylester.

9. A skin preparation, according to any one of claims 1–3, or 5–8 wherein said preparation is a cream or oil.

10. A method for protecting the skin of mammals, comprising the step of applying to the skin of the mammal a preparation as claimed in any one of claims 1–9.

11. A method of using an ALA derivative to manufacture a skin preparation with anti-carcinogenic and sun-protection effect comprising the steps of adding an ALA-derivative to a commercial base, said base having a UVB-absorbent agent and a UVA-absorbent agent.

12. The method according to claim 11, wherein the UVB-absorbent agent and the UVA-absorbent agent are selected from the group consisting of oxybenzenes, methoxycinnamates, salicylates, benzophenone derivatives, phenylbenzidine derivatives and methoxybenzoyl derivatives and physical filters, such as titanium dioxide, zinc oxide, calcium carbonate, kaolin, magnesium oxide, iron oxide or talc.

13. The method according to claim 12, wherein the ALA derivative is an ester derivative or an amino derivative.

14. The method according to claim 12, wherein the ALA derivative is selected from the group consisting of ALA-methylester, ALA-butylester and ALA-hexylester.

15. The method according to claim 13 or 14, wherein the ALA-derivative is from 0.02% to 0.4% by weight of the product.

* * * * *